(12) United States Patent
Naniki et al.

(10) Patent No.: US 10,029,241 B2
(45) Date of Patent: Jul. 24, 2018

(54) METHOD FOR PRODUCING CATALYST FOR CYCLIC CARBONATE SYNTHESIS

(71) Applicants: MARUZEN PETROCHEMICAL CO., LTD., Chuo-ku (JP); NATIONAL INSTITUTE OF ADVANCED INDUSTRIAL SCIENCE AND TECHNOLOGY, Chiyoda-ku (JP)

(72) Inventors: Takashi Naniki, Ichihara (JP); Toshikazu Takahashi, Tsukuba (JP); Hiroyuki Yasuda, Tsukuba (JP); Shouji Yamamoto, Tsukuba (JP)

(73) Assignees: MARUZEN PETROCHEMICAL CO., LTD., Chuo-ku (JP); National Institute of Advanced Industrial Science and Technology, Chiyoda-ku (JP)

( * ) Notice: Subject to any disclaimer, the term of this patent is extended or adjusted under 35 U.S.C. 154(b) by 0 days.

(21) Appl. No.: 14/786,326

(22) PCT Filed: Apr. 22, 2014

(86) PCT No.: PCT/JP2014/061278
§ 371 (c)(1),
(2) Date: Oct. 22, 2015

(87) PCT Pub. No.: WO2014/175262
PCT Pub. Date: Oct. 30, 2014

(65) Prior Publication Data
US 2016/0067695 A1    Mar. 10, 2016

(30) Foreign Application Priority Data

Apr. 23, 2013 (JP) ................. 2013-090238

(51) Int. Cl.
| | | |
|---|---|---|
| *B01J 31/02* | (2006.01) | |
| *C07D 317/36* | (2006.01) | |
| *C07D 317/38* | (2006.01) | |
| *B01J 21/08* | (2006.01) | |
| *B01J 27/08* | (2006.01) | |
| *B01J 27/16* | (2006.01) | |
| *B01J 27/182* | (2006.01) | |
| *B01J 35/10* | (2006.01) | |
| *B01J 31/26* | (2006.01) | |
| *B01J 31/06* | (2006.01) | |

(52) U.S. Cl.
CPC ........... *B01J 31/0268* (2013.01); *B01J 21/08* (2013.01); *B01J 27/08* (2013.01); *B01J 27/16* (2013.01); *B01J 27/182* (2013.01); *B01J 31/0267* (2013.01); *B01J 31/0269* (2013.01); *B01J 31/069* (2013.01); *B01J 31/26* (2013.01); *B01J 35/1019* (2013.01); *B01J 35/1023* (2013.01); *B01J 35/1061* (2013.01); *C07D 317/36* (2013.01); *C07D 317/38* (2013.01); *B01J 2231/341* (2013.01)

(58) Field of Classification Search
CPC .................................................. B01J 31/0268
USPC ............................................................ 549/23
See application file for complete search history.

(56) References Cited

U.S. PATENT DOCUMENTS

| | | |
|---|---|---|
| 4,314,945 A | 2/1982 | McMullen et al. |
| 2008/0214386 A1 | 9/2008 | Takahashi et al. |
| 2013/0317179 A1 | 11/2013 | Chen et al. |

FOREIGN PATENT DOCUMENTS

| | | |
|---|---|---|
| JP | 55 145623 | 11/1980 |
| JP | 63 17072 | 4/1988 |
| JP | 2007 209926 | 8/2007 |
| JP | 2008 296066 | 12/2008 |
| WO | 2005 084801 | 9/2005 |
| WO | 2014/175261 | 10/2014 |
| WO | 2015/008854 | 1/2015 |
| WO | 2015008853 | 1/2015 |

OTHER PUBLICATIONS

Hackh's Chem. Dictionary, 4the edition (1969), pp. 610.*
International Search Report dated Aug. 5, 2014 in PCT/JP2014/061278 filed Apr. 22, 2014.
Takahashi, T. et al., "Synergistic hybrid catalyst for cyclic carbonate synthesis: Remarkable acceleration caused by immobilization of homogeneous catalyst on silica", Chem. Commun., pp. 1664-1666, 2006.
Sakai, T et al., "Highly active and robust organic-inorganic hybrid catalyst for the synthesis of cyclic carbonates from carbon dioxide and epoxides", Green Chemistry, vol. 10, pp. 337-341, 2008.
U.S. Appl. No. 14/786,326, filed Oct. 22, 2015 Naniki et al.
U.S. Appl. No. 14/786,455, filed Oct. 22, 2015 Yamazaki et al.
U.S. Appl. No. 14/786,334, filed Oct. 22, 2015 Takahashi et al.
U.S. Office Action dated Jun. 6, 2016 in connection U.S. Appl. No. 14/786,455.
Pietro Tundo, et al. "Synthesis, Catalytic Activity and Behavior of Phase-Transfer Catalysts Supported on Silica Gel. Strong Influence of Substrate Adsorption on the Polar Polymetric Matrix on the Efficiency of the Immobilized Phosphonium Salts", J. Am. Chem. Soc., 101:22, pp. 6606-6613. (Oct. 24, 1979).
Aerosil Product Information (Aug. 2011).
E. M. Arnett, et al. "Solvent Effects in Organic Chemistry. V. Molecules, Ions, and Transitions States in Aqueous Ethanol", J. Chem. Soc., 87(7), pp. 1541-1553. (Apr. 5, 1965).

(Continued)

*Primary Examiner* — Taofiq A Solola
(74) *Attorney, Agent, or Firm* — Oblon, McClelland, Maier & Neustadt, L.L.P.

(57) ABSTRACT

A method for easily producing a heterogeneous catalyst having excellent catalytic activity at a low cost is provided. The heterogeneous catalyst is used for the purpose of synthesizing a cyclic carbonate by reacting an epoxide and carbon dioxide. A catalyst obtained by this production method and a method for synthesizing a cyclic carbonate with use of this catalyst are also provided.

13 Claims, 1 Drawing Sheet

(56) References Cited

OTHER PUBLICATIONS

"Research Techniques in Organic Chemistry" (Bates, Robert B.; Schaefer, John P. (1971), Prentice-Hall, Inc., Englewood Cliffs, N.J. p. 16-19.
Supplementary European Search Report dated Nov. 17, 2016 in connection with corresponding European Application No. 14788232.8, filed Apr. 22, 2014.

* cited by examiner

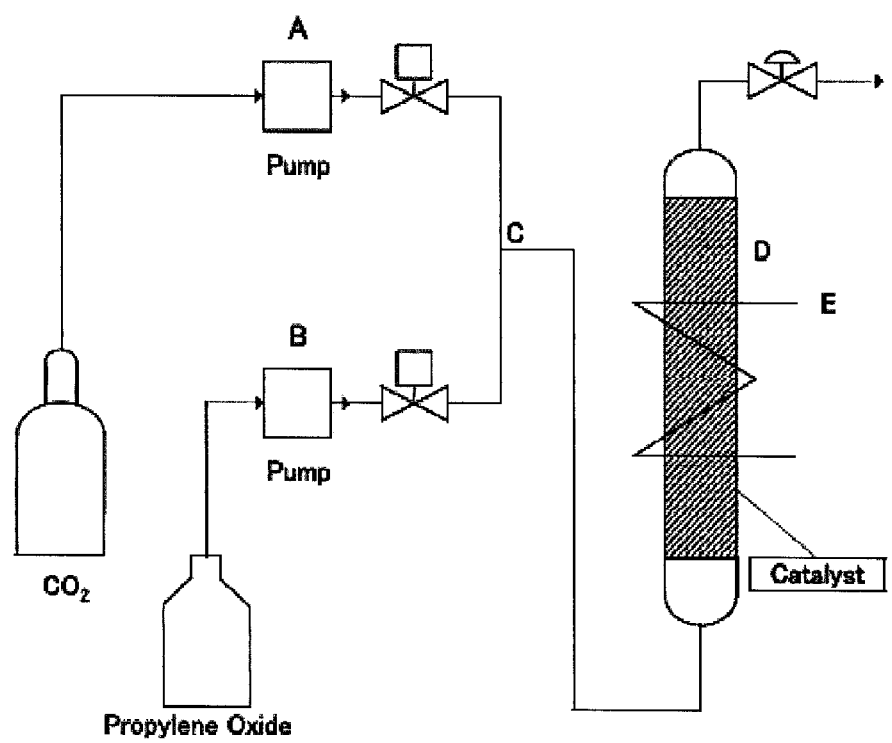

METHOD FOR PRODUCING CATALYST FOR CYCLIC CARBONATE SYNTHESIS

TECHNICAL FIELD

The present invention relates to a method for producing a catalyst used to synthesize a cyclic carbonate, a catalyst obtained by this method, and a method for synthesizing a cyclic carbonate with use of this catalyst.

BACKGROUND ART

A cyclic carbonate is one of important compounds used for many applications as organic solvents, synthetic fiber-processing agents, materials for medicines, cosmetic additives, electrolyte solvents for lithium cells, and further as intermediates for synthesizing alkylene glycols and dialkyl carbonates.

Heretofore, such a cyclic carbonate is synthesized by reacting an epoxide and carbon dioxide in the presence of a homogeneous catalyst under a suitable pressure. As the homogeneous catalyst, halides of alkali metals (Patent Literature 1) and onium salts such as quaternary ammonium salts (Patent Literature 2) are well known for a long time and are used industrially.

However, when such a homogeneous catalyst is used, it generally requires a separation procedure, such as distillation of the catalyst from the reaction mixture. Thus, not only the production process is complicated but also some problems such as degradation of catalyst and formation of byproducts may occur during separation step.

CITATION LIST

Patent Literature

Patent Literature 1: JP S63-17072 B
Patent Literature 2: JP S55-145623 A
Patent Literature 3: WO 2005/084801 A
Patent Literature 4: JP 2008-296066 A

SUMMARY OF INVENTION

Technical Problem

Then, for the purpose of simplifying the separation process of catalysts, a heterogeneous catalyst which has immobilized a quaternary phosphonium group having a halide ion as the counterion to a carrier such as silica gel has been proposed (Patent Literature 3). This catalyst can be produced by reacting a trialkyl phosphine and a commercially available carrier in which a haloalkyl chain is immobilized to a silica gel via a covalent bond to form a quaternary phosphonium product.

However, the production method disclosed in Patent Literature 3 needs the quaternary phosphonium formation reaction at a high temperature for a long period, and a considerable amount of the haloalkyl chains remains unreacted with the phosphine even if the reaction is performed for a long period.

Without using a commercially available product, a silica gel in which a haloalkyl chain or a haloaryl chain is immobilized by a covalent bond can be obtained by reacting a silane compound such as 3-bromopropyltriethoxysilane with a silica gel in toluene under reflux conditions. However, the reaction speed in this reaction is decreased generally when the concentration of the silane compound is decreased. Therefore, a large excess amount of the silane compound (several times to several ten times the amount of the silica gel) is used in order to introduce a sufficient amount of the haloalkyl chain, or the repeated operations of distilling the reaction solution so as to raise the concentration of the silane compound are employed.

However, when a large amount of the silane compound is used, not only a condensate between the silane compounds becomes easy to be formed, resulting in decrease of the catalytic activity, but also wastes in the manufacturing process of the catalyst increase, resulting in the reduction of production efficiency for the catalyst. In addition, a method for promoting the reaction while distilling off the solvent requires not only a complicated reaction system but also an increased number of steps.

Further, as a method for easily producing a catalyst in which a quaternary phosphonium having a halide ion as the counterion is immobilized as described in Patent Literature 3, there has been proposed a method of preliminarily reacting 3-bromopropyltriethoxysilane and diphenyl monoalkyl phosphine to form a quaternary phosphonium and then modifying the surface of a carrier with use of this quaternary phosphonium compound as a catalyst crosslinking agent (Patent Literature 4).

However, when a silane compound obtained by the reaction with a diphenylmonoalkylphosphine to form a quaternary phosphonium is used as a catalyst crosslinking agent, the amount of the silane compound that binds to the silica gel surface is limited due to the steric hindrance. Thus, the supported amount of halogen and phosphorus is far from sufficient. Moreover, since a byproduct is formed as a result of the reaction between the quaternary phosphonium salt and the silane compound in the presence of silica gel, it is difficult to produce a catalyst exhibiting an activity that is corresponding to the amount of the phosphonium salt and the silane compound used.

Accordingly, the present invention relates to a method for easily producing a heterogeneous catalyst having excellent catalytic activity at a low cost, said heterogeneous catalyst being used for the purpose of synthesizing a cyclic carbonate by subjecting to a reaction an epoxide with carbon dioxide; a catalyst which is obtained by this production method; and a method for synthesizing a cyclic carbonate with use of this catalyst.

Solution to Problem

Then, as a result of extensive studies, the present inventors have found that a heterogeneous catalyst obtained by reacting a silane compound having a haloalkyl group or a haloaryl group with a silica gel having an amount of adsorbed water of 1% by mass or less, thereby obtaining a catalyst precursor having a haloalkyl group or a haloaryl group and then reacting the catalyst precursor with a tertiary phosphine, wherein the molar ratio of the halogen content to the phosphorus content, [halogen]/[phosphorus] is from 0.8 to 1.6, can be easily produced at a low cost, and that such a catalyst shows an excellent catalytic activity in synthesizing a cyclic carbonate by reacting an epoxide with carbon dioxide. The present invention has been completed based on these findings.

That is, the present invention provides a method for producing a catalyst that is used for the purpose of synthesizing a cyclic carbonate by reacting an epoxide and carbon dioxide. The method includes the following steps (a) and (b):

(a) a step of obtaining a catalyst precursor having a haloalkyl group or a haloaryl group, by subjecting to a reaction a silane compound having a haloalkyl group or a haloaryl group and a silica gel having an amount of adsorbed water of 1% by mass or less and (b) a step of obtaining a catalyst for cyclic carbonate synthesis, by subjecting to a reaction the catalyst precursor obtained in step (a) and a tertiary phosphine, wherein the molar ratio of the halogen content to the phosphorus content, namely [halogen]/[phosphorus] is from 0.8 to 1.6.

Further, the present invention provides the catalyst obtained by the production method, the catalyst being used for the purpose of synthesizing a cyclic carbonate by reacting an epoxide with carbon dioxide.

In addition, the present invention provides a method for synthesizing a cyclic carbonate, comprising reacting an epoxide with carbon dioxide in the presence of the catalyst.

Further, the present invention provides a method for synthesizing a cyclic carbonate, comprising reacting an epoxide with carbon dioxide with use of a silica gel-immobilized phosphonium salt halide as a catalyst containing a quaternary phosphonium group having a halide anion as the counterion, wherein the catalyst has the halogen content of from 0.25 to 0.8 mmol per 1 g of the catalyst and has the molar ratio of the halogen content to the phosphorus content [halogen/phosphorus] of from 1.0 to 1.6.

Advantageous Effects of Invention

According to the production method of the present invention, a heterogeneous catalyst showing an excellent catalytic activity and being capable of synthesizing a cyclic carbonate in a high conversion rate and a high yield can be easily produced at a low cost.

Thus, the catalyst of the present invention is useful as a catalyst for use in synthesizing a cyclic carbonate by reacting an epoxide with carbon dioxide. Further, according to the synthesis method of a cyclic carbonate of the present invention, the cyclic carbonate can be synthesized in a high conversion rate and a high yield.

BRIEF DESCRIPTION OF DRAWINGS

FIG. 1 is a schematic view showing an example of an apparatus used in the synthesis method of a cyclic carbonate according to the present invention.

DESCRIPTION OF EMBODIMENTS

<Production Method of Catalyst for Synthesizing Cyclic Carbonate>

The production method of a catalyst for use in synthesizing a cyclic carbonate by reacting an epoxide with carbon dioxide according to the present invention comprises the above steps (a) and (b).

[Step (a)]

Step (a) is a step of obtaining a catalyst precursor having a haloalkyl group or a haloaryl group by reacting a silane compound having a haloalkyl group or a haloaryl group with a silica gel having an amount of adsorbed water of 1% by mass or less.

The amount of adsorbed water of the silica gel used in step (a) is 1% by mass or less, and from the viewpoint of suppressing the occurrence of byproducts in the cyclic carbonate synthesis, such amount is preferably from 0.001 to 0.9% by mass, more preferably from 0.01 to 0.85% by mass, furthermore preferably from 0.25 to 0.75% by mass, especially preferably from 0.3 to 0.6% by mass. By using a silica gel having an amount of adsorbed water of such a range, it is easy to control the silica gel content and the phosphorus content in the catalyst. Also, by adjusting the amount of adsorbed water to 1% by mass or less, surface silanol is suppressed to prevent halogen from being excessively supported, thereby improving the catalytic activity.

Here, the amount of adsorbed water refers to an amount of water present in the silica gel pores and it may be measured by a thermogravimetry device.

Moreover, the amount of adsorbed water can be controlled in the above range by appropriately adjusting it prior to step (a), and such a method includes drying treatment of silica gel and addition of water to silica gel.

The drying method of the silica gel is not particularly limited and includes, for example, a method of heating under reduced pressure or in a stream of dry air (or inert gas) and a method of refluxing treatment using a Dean-Stark trap. The solvent used in the refluxing treatment is not particularly limited as long as water can be removed azeotropically; however, from the viewpoint of suppressing the intake of water due to substitution of the solvent, it is preferable to adopt such a solvent as the solvent to be used in step (a) without any substitution.

Furthermore, silica gel may be treated with an acid such as hydrochloric acid before drying.

Further, the average pore diameter of the silica gel is preferably from 3.5 to 50 nm, more preferably from 3.5 to 25 nm, furthermore preferably from 5 to 20 nm, especially preferably from 6 to 15 nm, in view of the catalytic activity and the prevention of the occurrence of byproducts in the synthesis of cyclic carbonates. By adjusting the average pore diameter to 3.5 nm or more, it is possible to easily introduce a tertiary phosphine into the pores and it is also possible to further suppress agglomeration of the phosphonium salt in the vicinity of the pore entrance, as well as suppress clogging of the pores.

In addition, the specific surface area of the silica gel is preferably from 80 to 2,000 m²/g, more preferably from 100 to 1,000 m²/g, further more preferably from 150 to 750 m²/g.

Further, the silica gel is preferably in the shape of particles from the viewpoint of handling properties during separation and recovery processes, etc. The shape of such particles is not particularly limited, and includes, for example, crushed shape, particle shape, bead shape, tablet shape, pellet shape, cylindrical shape, and powder shape, and may be an irregular one. If the silica gel is in the shape of beads, the particle diameter is preferably from 0.1 to 10 mm, more preferably from 0.2 to 8 mm, further more preferably from 0.5 to 5.0 mm. Also, if the silica gel is in the shape of powder, the particle diameter is preferably from 30 to 5,000 mesh, more preferably from 100 to 1,000 mesh.

The average pore diameter, specific surface area, and particle diameter of the silica gel can be measured by, for example, a specific surface area/pore distribution measuring apparatus.

In addition, as the silane compound having a haloalkyl group or a haloaryl group used in step (a), those represented by the following formula (1) are preferred. The silane compounds may be used alone or in combination of two or more thereof.

$$X-R^1-Si(OR^2)_3 \tag{1}$$

In the formula (1), $R^1$ represents a linear or branched alkylene group having 2 to 8 of carbon atom, an arylene group, an alkarylene group, an arylenealkylene group or an alkylenearylene group; $R^2$ represents an alkyl group having 1 to 4 of carbon atom; and X represents a halogen atom.

In the formula (1), the linear or branched alkylene group having 2 to 8 of carbon atom represented by $R^1$ includes, for example, ethylene group, trimethylene group, propylene group, tetramethylene group, pentamethylene group, hexamethylene group, heptamethylene group, and octamethylene group.

Also, the arylene group represented by $R^1$ is preferably an arylene group having 6 to 10 of carbon atom, such as phenylene group and tolylene group.

In addition, the alkarylene group represented by $R^1$ is preferably an alkarylene group having 8 to 10 of carbon atom, such as xylylene group.

Moreover, the arylenealkylene group represented by $R^1$ is preferably an arylenealkylene group having 6 to 10 of carbon atom, such as phenylene methylene group and phenylene ethylene group.

Furthermore, the alkylenearylene group represented by $R^1$ is preferably an alkylenearylene group having 6 to 10 of carbon atom, such as methylene phenylene group and ethylene phenylene group.

Of these, preferred is a linear or branched alkylene group having 2 to 8 of carbon atom, more preferred is a linear or branched alkylene group having 2 to 6 of carbon atom, and especially preferred is a trimethylene group.

In the formula (1), the alkyl group having 1 to 4 of carbon atom represented by $R^2$ includes, for example, methyl group, ethyl group, propyl group, and butyl group, among which preferred are methyl group and ethyl group, and more preferred is methyl group.

The halogen atom represented by X in the formula (1) includes chlorine atom, bromine atom, and iodine atom, among which bromine atom is preferable.

Specific examples of the silane compounds represented by the formula (1) having a haloalkyl group include, for example, a halo-$C_{2-8}$ alkyl-trimethoxysilane, a halo-$C_{2-8}$ alkyl-triethoxysilane, a halo-$C_{2-8}$ alkyl-tripropoxysilane, a haloalkylaryl trimethoxysilane, a haloalkylaryl triethoxysilane, a haloalkylaryl tripropoxysilane, a haloalkylaralkyl trimethoxysilane, a haloalkylaralkyl triethoxysilane, and a haloalkylaralkyl tripropoxysilane.

The halo-$C_{2-8}$ alkyl-trimethoxysilane includes, for example, 2-chloroethyltrimethoxysilane, 2-bromoethyltrimethoxysilane, 2-iodoethyltrimethoxysilane, 3-chloropropyltrimethoxysilane, 3-bromopropyltrimethoxysilane, 3-iodopropyltrimethoxysilane, 4-chlorobutyltrimethoxysilane, 4-bromobutyltrimethoxysilane, 4-iodobutyltrimethoxysilane, 5-chloropentyltrimethoxysilane, 5-bromopentyltrimethoxysilane, 5-iodopentyltrimethoxysilane, 6-chlorohexyltrimethoxysilane, 6-bromohexyltrimethoxysilane, 6-iodohexyltrimethoxysilane, 7-chloroheptyltrimethoxysilane, 7-bromoheptyltrimethoxysilane, 7-iodoheptyltrimethoxysilane, 8-chlorooctyltrimethoxysilane, 8-bromooctyltrimethoxysilane, and 8-iodooctyltrimethoxysilane.

Moreover, the halo-$C_{2-8}$ alkyl-triethoxysilane includes, for example, 2-chloroethyltriethoxysilane, 2-bromoethyltriethoxysilane, 2-iodoethyltriethoxysilane, 3-chloropropyltriethoxysilane, 3-bromopropyltriethoxysilane, 3-iodopropyltriethoxysilane, 4-chlorobutyltriethoxysilane, 4-bromobutyltriethoxysilane, 4-iodobutyltriethoxysilane, 5-chloropentyltriethoxysilane, 5-bromopentyltriethoxysilane, 5-iodopentyltriethoxysilane, 6-chlorohexyltriethoxysilane, 6-bromohexyltriethoxysilane, 6-iodohexyltriethoxysilane, 7-chloroheptyltriethoxysilane, 7-bromoheptyltriethoxysilane, 7-iodoheptyltriethoxysilane, 8-chlorooctyltriethoxysilane, 8-bromooctyltriethoxysilane, and 8-iodooctyltriethoxysilane.

Moreover, the halo-$C_{2-8}$ alkyl-tripropoxysilane includes, for example, 2-chloroethyltripropoxysilane, 2-bromoethyltripropoxysilane, 2-iodoethyltripropoxysilane, 3-chloropropyltripropoxysilane, 3-bromopropyltripropoxysilane, 3-iodopropyltripropoxysilane, 4-chlorobutyltripropoxysilane, 4-bromobutyltripropoxysilane, 4-iodobutyltripropoxysilane, 5-chloropentyltripropoxysilane, 5-bromopentyltripropoxysilane, 5-iodopentyltripropoxysilane, 6-chlorohexyltripropoxysilane, 6-bromohexyltripropoxysilane, 6-iodohexyltripropoxysilane, 7-chloroheptyltripropoxysilane, 7-bromoheptyltripropoxysilane, 7-iodoheptyltripropoxysilane, 8-chlorooctyltripropoxysilane, 8-bromooctyltripropoxysilane, and 8-iodooctyltripropoxysilane.

The haloalkylaryltrimethoxysilane includes, for example,
p-chloromethylphenyltrimethoxysilane,
p-(2-chloroethyl)phenyltrimethoxysilane,
p-bromomethylphenyltrimethoxysilane,
p-(2-bromoethyl)phenyltrimethoxysilane,
p-iodomethylphenyltrimethoxysilane, and
p-(2-iodoethyl)phenyltrimethoxysilane.

Further, the haloalkylaryltriethoxysilane includes, for example, p-chloromethylphenyltriethoxysilane, p-(2-chloroethyl)phenyltriethoxysilane, p-bromomethylphenyltriethoxysilane, p-(2-bromoethyl)phenyltriethoxysilane, p-iodomethylphenyltriethoxysilane, and p-(2-iodoethyl)phenyltriethoxysilane.

In addition, the haloalkylaryltripropoxysilane includes, for example, p-chloromethylphenyltripropoxysilane, p-(2-chloroethyl)phenyltripropoxysilane, p-bromomethylphenyltripropoxysilane, p-(2-bromoethyl)phenyltripropoxysilane, p-iodomethylphenyltripropoxysilane, and p-(2-iodoethyl)phenyltripropoxysilane.

The haloalkylaralkyltrimethoxysilane includes, for example,
p-chloromethylbenzyltrimethoxysilane,
p-bromomethylbenzyltrimethoxysilane, and
p-iodomethylbenzyltrimethoxysilane.

Further, the haloalkylaralkyltriethoxysilane includes, for example, p-chloromethylbenzyltriethoxysilane, p-bromomethylbenzyltriethoxysilane, and p-iodomethylbenzyltriethoxysilane.

In addition, the haloalkylaralkyltripropoxysilane includes, for example, p-chloromethylbenzyltripropoxysilane, p-bromomethylbenzyltripropoxysilane, and p-iodomethylbenzyltripropoxysilane.

Specific examples of the silane compounds represented by the formula (1) having a haloaryl group include, for example, a haloaryltrialkoxysilane and a haloaralkyltrialkoxysilane.

The haloaryltrialkoxysilane includes p-chlorophenyltrimethoxysilane, p-bromophenyltrimethoxysilane, p-chlorophenyltriethoxysilane, p-bromophenyltriethoxysilane, p-chlorophenyltripropoxysilane, and p-bromophenyltripropoxysilane.

The haloaralkyltrialkoxysilane includes, for example, p-chlorobenzyltrimethoxysilane, p-bromobenzyltrimethoxysilane, p-iodobenzyltrimethoxysilane, p-chlorobenzyltriethoxysilane, p-bromobenzyltriethoxysilane, p-iodobenzyltriethoxysilane, p-chlorobenzyltripropoxysilane, p-bromobenzyltripropoxysilane, and p-iodobenzyltripropoxysilane.

The amount used of the silane compound is preferably from 0.001 to 0.5 mole, more preferably from 0.01 to 0.1 mole, further more preferably from 0.02 to 0.08 mole, especially preferably from 0.025 to 0.06 mole, relative to 1 mole of silica gel from the viewpoint of catalytic activity and low cost production of the catalyst.

Moreover, step (a) is preferably carried out in a solvent, and a hydrocarbon solvent is preferred as such a solvent.

As the hydrocarbon solvent, there are exemplified aliphatic hydrocarbon solvents, aromatic hydrocarbon solvents, and alicyclic hydrocarbon solvents. Incidentally, the aliphatic hydrocarbon solvent may be any of normal paraffin solvents (such as n-dodecane) and isoparaffin solvents (such as isododecane). These solvents may be used alone or in combination of two or more thereof.

Among these hydrocarbon solvents, aromatic hydrocarbon solvents are preferred from the viewpoints of the reaction rate and the suppression of the occurrence of side reactions during the synthesis of cyclic carbonates. The aromatic hydrocarbon solvent includes, for example, toluene, xylene, and ethylbenzene, and xylene is more preferable from the viewpoint that an active catalyst can be efficiently obtained even with use of a small amount of the silane compound. Xylene may be any of o-xylene, m-xylene, p-xylene, and a mixture thereof, and may also contain ethylbenzene.

The amount used of the solvent is not particularly limited; however it is usually from 100 to 750 parts by mass, preferably from 100 to 500 parts by mass, more preferably from 200 to 300 parts by mass, per 100 parts by mass of silica gel.

Whereas the reaction temperature of step (a) is not particularly limited, it is preferably from 50 to 160° C., more preferably from 80 to 150° C., further more preferably from 100 to 140° C. It is possible to suppress the degradation of the supported silane compound by keeping the reaction temperature at 160° C. or less, while it is possible to increase the reaction rate by keeping the reaction temperature at 50° C. or more.

The reaction time in step (a) is not particularly limited; however, it is preferably from 1 to 30 hours, more preferably from 3 to 28 hours, particularly preferably from 5 to 26 hours.

The halogen content in the catalyst precursor having a haloalkyl group or a haloaryl group, obtained in step (a), is preferably 1.0 mmol or less, more preferably from 0.1 to 1.0 mmol, furthermore preferably from 0.2 to 0.95 mmol, especially preferably from 0.3 to 0.9 mmol, per 1 g of the catalyst precursor from the viewpoint of catalytic activity. By adjusting the amount used of the silane compound having a haloalkyl group or a haloaryl group or by using a silica gel whose adsorbed water content is prepared in an amount of 1% by mass or less, the halogen content can be controlled within the above range.

The halogen content can be measured in the same manner as in Examples described below.

[Step (b)]

Step (b) is a step of obtaining a catalyst for cyclic carbonate synthesis, by subjecting to a reaction the catalyst precursor obtained in step (a) with a tertiary phosphine, in which the molar ratio of the halogen content to the phosphorus content, namely [halogen]/[phosphorus] is from 0.8 to 1.6. By reacting the catalyst precursor and a tertiary phosphine, a haloalkyl group or a haloaryl group of the catalyst precursor is converted to a quaternary phosphonium group having a halide anion as the counterion. Thus, the catalyst for cyclic carbonate synthesis contains a quaternary phosphonium group having a halide anion as the counterion.

As the tertiary phosphine used in step (b), those represented by the following formula (2) are preferable. The tertiary phosphines may be used alone or in combination of two or more thereof.

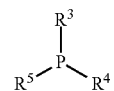

(2)

In the formula (2), $R^3$ to $R^5$ each independently represents an alkyl group having 1 to 8 of carbon atom, an aryl group, an aralkyl group, an alkokyalkyl group or an alkoky-substituted aryl group, or a group in which one or more hydrogen atoms contained in these groups are substituted with a hetero atom-containing group.

In the formula (2), the alkyl group having 1 to 8 of carbon atom represented by $R^3$ to $R^5$ may be linear, branched, or circular, and includes, for example, methyl group, ethyl group, propyl group, isopropyl group, butyl group, isobutyl group, pentyl group, hexyl group, heptyl group, octyl group, and cyclohexyl group.

Further, the aryl group represented by $R^3$ to $R^5$ is preferably an aryl group having 6 to 10 of carbon atom, such as phenyl group, tolyl group, xylyl group, and naphthyl group.

Moreover, the aralkyl group represented by $R^3$ to $R^5$ is preferably an aralkyl group having 7 to 12 of carbon atom, such as benzyl group.

In addition, the alkoxyalkyl group represented by $R^3$ to $R^5$ is preferably an alkoxyalkyl group having 2 to 8 of carbon atom, such as methoxyethyl group.

The aryl group having an alkoxy group as a substituent, represented by $R^3$ to $R^5$, is preferably an alkoxyaryl group having 7 to 14 of carbon atom, such as methoxyphenyl group and dimethoxyphenyl group. Further, whereas the number and position of the alkoxy group of the aryl group may be arbitrary, the number of the alkoxy groups is preferably from 1 to 4, more preferably 1 or 2.

Incidentally, one or more hydrogen atoms contained in the alkyl group having 1 to 8 of carbon atom, aryl group, aralkyl group, alkoxyalkyl group and alkoxy-substituted aryl group described above may be substituted by a group containing a hetero atom. The hetero atom includes, for example, a nitrogen atom, an oxygen atom, a phosphorus atom, a sulfur atom, and a halogen atom (such as a fluorine atom).

Examples of the group containing the hetero atom includes, for example, a nitrogen-containing group (such as amino group, hydrazino group, nitro group, cyano group, isocyano group, and amidino grouo); an oxygen-containing group (such as alkanoyl group, carboxy group, alkoxycarbonyl group, and hydroxy group); a phosphorus-containing group (such as phosphanyl group, phosphono group, and phosphinyl group); and a sulfur-containing groups (such as sulfo group, sulfanyl group, alkylsulfanyl group, alkylsulfonyl group, alkylsulfonylamino group, alkylaminosulfonyl group, alkylsulfinyl group, alkylaminosulfinyl group, alkylsulfinylamino group, and thiocarboxy group).

Among the groups represented by $R^3$ to $R^5$ as described above, an alkyl group having 1 to 8 of carbon atom is preferable, a linear or branched alkyl group having 1 to 8 of carbon atom is more preferable, a linear or branched alkyl group having 1 to 4 of carbon atom is further more preferable, and butyl group is especially preferable.

Specific examples of the compound represented by the formula (2) include tri-$C_{1-8}$-alkylphosphine, triarylphosphine, diaryl-$C_{1-8}$-alkylphosphine, aryl-di-$C_{1-8}$-alkylphosphine, triaralkylphosphine, diaralkyl-$C_{1-8}$-alkylphosphine, diaralkylarylphosphine, aralkyl-di-$C_{1-8}$-alkylphosphine, aralkyldiarylphosphine, tris(alkoxyaryl)phosphine, bis(alkoxyaryl)$C_{1-8}$-alkylphosphine, bis(alkoxyaryl)arylphosphine, bis(alkoxyaryl)aralkylphosphine, (alkoxyaryl)di-$C_{1-8}$-alkylphosphine, (dialkoxyaryl)di-$C_{1-8}$-alkylphosphine, alkoxyaryldiarylphosphine, (dialkoxyaryl)diarylphosphine, alkoxyaryldiaralkylphosphine, and (dialkoxyaryl)diaralkylphosphine.

The tri-$C_{1-8}$-alkylphosphine includes, for example, trimethylphosphine, triethylphosphine, tripropylphosphine, triisopropylphosphine, tri-n-butylphosphine, triisobutylphosphine, tripentylphosphine, trihexylphosphine, triheptylphosphine, trioctylphosphine, tricyclohexylphosphine, dimethylethylphosphine, dimethylpropylphosphine, dimethylisopropylphosphine, dimethyl-n-butylphosphine, dimethylisobutylphosphine, dimethylpentylphosphine, dimethylhexylphosphine, dimethylheptylphosphine, dimethyloctylphosphine, dimethylcyclohexylphosphine, diethylmethylphosphine, diethylpropylphosphine, diethylisopropylphosphine, diethyl-n-butylphosphine, diethylisobutylphosphine, diethylpentylphosphine, diethylhexylphosphine, diethylheptylphosphine, diethyloctylphosphine, diethylcyclohexylphosphine,
dipropylmethylphosphine, dipropylethylphosphine, dipropylisopropylphosphine, dipropyl-n-butylphosphine, dipropylisobutylphosphine, dipropylpentylphosphine, dipropylhexylphosphine, dipropylheptylphosphine, dipropyloctylphosphine, dipropylcyclohexylphosphine, diisopropylmethylphosphine, diisopropylethylphosphine, diisopropylpropylphosphine, diisopropyl-n-butylphosphine, diisopropylisobutylphosphine, diisopropylpentylphosphine, diisopropylhexylphosphine, diisopropylheptylphosphine, diisopropyloctylphosphine, diisopropylcyclohexylphosphine, di-n-butylmethylphosphine, di-n-butylethylphosphine, di-n-butylpropylphosphine, di-n-butylisopropylphosphine, di-n-butylisobutylphosphine, di-n-butylpentylphosphine, di-n-butylhexylphosphine, di-n-butylheptylphosphine, di-n-butylethyloctylphosphine, di-n-butylcyclohexylphosphine,
diisobutylmethylphosphine, diisobutylethylphosphine, diisobutylpropylphosphine, diisobutylisopropylphosphine, diisobutyl-n-butylphosphine, diisobutylpentylphosphine, diisobutylhexylphosphine, diisobutylheptylphosphine, diisobutyloctylphosphine, diisobutylcyclohexylphosphine, dipentylmethylphosphine, dipentylethylphosphine, dipentylpropylphosphine, dipentylisopropylphosphine, dipentyl-n-butylphosphine, dipentylisobutylphosphine, dipentylhexylphosphine, dipentylheptylphosphine, dipentyloctylphosphine, dipentylcyclohexylphosphine, dihexylmethylphosphine, dihexylethylphosphine, dihexylpropylphosphine, dihexylisopropylphosphine, dihexyl-n-butylphosphine, dihexylisobutylphosphine, dihexylpentylphosphine, dihexylheptylphosphine, dihexyloctylphosphine, dihexylcyclohexylphosphine,
diheptylmethylphosphine, diheptylethylphosphine, diheptylpropylphosphine, diheptylisopropylphosphine, diheptyl-n-butylphosphine, diheptylisobutylphosphine, diheptylpentylphosphine, diheptylhexylphosphine, diheptyloctylphosphine, diheptylcyclohexylphosphine, dioctylmethylphosphine, dioctylethylphosphine, dioctylpropylphosphine, dioctylisopropylphosphine, dioctyl-n-butylphosphine, dioctylisobutylphosphine, dioctylpentylphosphine, dioctylhexylphosphine, dioctylheptylphosphine, dioctylcyclohexylphosphine, dicyclohexylmethylphosphine, dicyclohexylethylphosphine, dicyclohexylpropylphosphine, dicyclohexylisopropylphosphine, dicyclohexyl-n-butylphosphine, dicyclohexylisobutylphosphine, dicyclohexylpentylphosphine, dicyclohexylhexylphosphine, dicyclohexylheptylphosphine, and dicyclohexyloctylphosphine.

The triarylphosphine includes triphenylphosphine, tritolylphosphine, and trixylylphosphine.

The diaryl-$C_{1-8}$-alkylphosphine includes, for example, diphenylmethylphosphine, diphenylethylphosphine, diphenylpropylphosphine, diphenylisopropylphosphine, diphenyl-n-butylphosphine, diphenylisobutylphosphine, diphenylpentylphosphine, diphenylhexylphosphine, diphenylheptylphosphine, diphenyloctylphosphine, diphenylcyclohexylphosphine, ditolylmethylphosphine, ditolylethylphosphine, ditolylpropylphosphine, ditolylisoproylphosphine, ditolyl-n-butylphosphine, ditolylisobutylphosphine, ditolylpentylphosphine, ditolylhexylphosphine, ditolylheptylphosphine, ditolyloctylphosphine, ditolylcyclohexylphosphine, dixylylmethylphosphine, dixylylethylphosphine, dixylylpropylphosphine, dixylylisopropylphosphine, dixylyl-n-butylphosphine, dixylylisobutylphosphine, dixylylpentylphosphine, dixylylhexylphosphine, dixylylheptylphosphine, dixylyloctylphosphine, and dixylylcyclohexylphosphine.

The aryl-di-$C_{1-8}$-alkylphosphine includes phenyldimethylphosphine, phenyldiethylphosphine, phenyldipropylphosphine, phenyldiisopropylphosphine, phenyldi-n-butylphosphine, phenyldiisobutylphosphine, phenyldipentylphosphine, phenyldihexylphosphine, phenyldiheptylphosphine, phenyldioctylphosphine, phenyldicyclohexylphosphine, tolyldimethylphosphine, tolyldiethylphosphine, tolyldipropylphosphine, tolyldiisopropylphosphine, tolyldi-n-butylphosphine, tolyldiisobutylphosphine, tolyldipentylphosphine, tolyldihexylphosphine, tolyldiheptylphosphine, tolyldioctylphosphine, tolyldicyclohexylphosphine, xylyldimethylphosphine, xylyldiethylphosphine, xylyldipropylphosphine, xylyldiisopropylphosphine, xylyldi-n-butylphosphine, xylyldiisobutylphosphine, xylyldipentylphosphine, xylyldihexylphosphine, xylyldiheptylphosphine, xylyldioctylphosphine, and xylyldicyclohexylphosphine.

The triaralkylphosphine includes tribenzylphosphine.

Moreover, the diaralkyl-$C_{1-8}$-alkylphosphine includes dibenzylmethylphosphine, dibenzylethylphosphine, dibenzylpropylphosphine, dibenzylisopropylphosphine, dibenzyl-n-butylphosphine, dibenzylisobutylphosphine, dibenzylpentylphosphine, dibenzylhexylphosphine, dibenzylheptylphosphine, dibenzyloctylphosphine, and dibenzylcyclohexylphosphine.

The diaralkylarylphosphine includes dibenzylphenylphosphine, dibenzyltolylphosphine, and dibenzylxylylphosphine.

The arakyldi-$C_{1-8}$-alkylphosphine includes benzyldimethylphosphine, benzyldiethylphosphine, benzyldipropylphosphine, benzyldiisopropylphosphine, benzyldi-n-butylphosphine, benzyldiisobutylphosphine, benzyldipentylphosphine, benzyldihexylphosphine, benzyldiheptylphosphine, benzyldioctylphosphine, and benzylcyclohexylphosphine.

The arakyldiarylphosphine includes benzyldiphenylphosphine, benzylditolylphosphine, and benzyldixylylphosphine.

The tris(alkoxyaryl)phosphine includes tris(2,6-dimethoxyphenyl)phosphine, tri-o-methoxyphenylphosphine, and tri-p-methoxyphenylphosphine.

The bis(alkoxyaryl)C$_{1-8}$-alkylphosphine includes
bis(2,6-dimethoxyphenyl)methylphosphine,
bis(2,6-dimethoxyphenyl)ethylphosphine,
bis(2,6-dimethoxyphenyl)propylphosphine,
bis(2,6-dimethoxyphenyl)isopropylphosphine,
bis(2,6-dimethoxyphenyl)n-butylphosphine,
bis(2,6-dimethoxyphenyl)isobutylphosphine,
bis(2,6-dimethoxyphenyl)pentylphosphine,
bis(2,6-dimethoxyphenyl)hexylphosphine,
bis(2,6-dimethoxyphenyl)heptylphosphine,
bis(2,6-dimethoxyphenyl)octylphosphine,
bis(2,6-dimethoxyphenyl)cyclohexylphosphine,
di-o-methoxyphenylmethylphosphine,
di-o-methoxyphenylethylphosphine,
di-o-methoxyphenylpropylphosphine,
di-o-methoxyphenylisopropylphosphine,
di-o-methoxyphenyl(n-butyl)phosphine,
di-o-methoxyphenylisobutylphosphine,
di-o-methoxyphenylpentylphosphine,
di-o-methoxyphenylhexylphosphine,
di-o-methoxyphenylheptylphosphine,
di-o-methoxyphenyloctylphosphine,
di-o-methoxyphenylcyclohexylphosphine,
di-p-methoxyphenylmethylphosphine,
di-p-methoxyphenylethylphosphine,
di-p-methoxyphenylmethylphosphine,
di-p-methoxyphenylethylphosphine,
di-p-methoxyphenylpropylphosphine,
di-p-methoxyphenylisopropylphosphine,
di-p-methoxyphenyl(n-butyl)phosphine,
di-p-methoxyphenylisobutylphosphine,
di-p-methoxyphenylpentylphosphine,
di-p-methoxyphenylhexylphosphine,
di-p-methoxyphenylheptylphosphine,
di-p-methoxyphenyloctylphosphine, and
di-p-methoxyphenylcyclohexylphosphine.

The bis(alkoxyaryl)arylphosphine includes:
bis(2,6-dimethoxyphenyl)phenylphosphine,
bis(2,6-dimethoxyphenyl)tolylphosphine,
bis(2,6-dimethoxyphenyl)xylylphosphine,
di-o-methoxyphenylphenylphosphine,
di-o-methoxyphenyltolylphosphine,
di-o-methoxyphenylxylylphosphine,
di-p-methoxyphenylphenylphosphine,
di-p-methoxyphenyltolylphosphine, and
di-p-methoxyphenylxylylphosphine.

The bis(alkoxyaryl)aralkylphosphine includes:
bis(2,6-dimethoxyphenyl)benzylphosphine,
di-o-methoxyphenylbenzylphosphine, and
di-p-methoxyphenylbenzylphosphine.

The (alkoxyaryl)di-C$_{1-8}$-alkylphosphine includes:
o-methoxyphenyldimethylphosphine,
o-methoxyphenyldiethylphosphine,
o-methoxyphenyldipropylphosphine,
o-methoxyphenyldiisopropylphosphine,
o-methoxyphenyldi(n-butyl)phosphine,
o-methoxyphenyldiisobutylphosphine,
o-methoxyphenyldipentylphosphine,
o-methoxyphenyldihexylphosphine,
o-methoxyphenyldiheptylphosphine,
o-methoxyphenyldioctylphosphine,
o-methoxyphenyldicyclohexylphosphine,
p-methoxyphenyldimethylphosphine,
p-methoxyphenyldiethylphosphine,
p-methoxyphenyldipropylphosphine,
p-methoxyphenyldiisopropylphosphine,
p-methoxyphenyldi-n-butylphosphine,
p-methoxyphenyldiisobutylphosphine,
p-methoxyphenyldipentylphosphine,
p-methoxyphenyldihexylphosphine,
p-methoxyphenyldiheptylphosphine,
p-methoxyphenyldioctylphosphine, and
p-methoxyphenyldicyclohexylphosphine.

The (dialkoxyaryl)di-C$_{1-8}$-alkylphosphine includes:
2,6-dimethoxyphenyldimethylphosphine,
2,6-dimethoxyphenyldiethylphosphine,
2,6-dimethoxyphenyldipropylphosphine,
2,6-dimethoxyphenyldiisopropylphosphine,
2,6-dimethoxyphenyl-di-n-butylphosphine,
2,6-dimethoxyphenyldiisobutylphosphine,
2,6-dimethoxyphenyldipentylphosphine,
2,6-dimethoxyphenyldihexylphosphine,
2,6-dimethoxyphenyldiheptylphosphine,
2,6-dimethoxyphenyldioctylphosphine, and
2,6-dimethoxyphenyldicyclohexylphosphine.

The alkoxyaryldiarylphosphine includes:
o-methoxyphenyldiphenylphosphine,
o-methoxyphenylditolylphosphine,
o-methoxyphenyldixylylphosphine,
p-methoxyphenyldiphenylphosphine,
p-methoxyphenylditolylphosphine, and
p-methoxyphenyldixylylphosphine.

The (dialkoxyaryl)diarylphosphine includes:
2,6-dimethoxyphenyldiphenylphosphine,
2,6-dimethoxyphenylditolylphosphine, and
2,6-dimethoxyphenyldixylylphosphine.

The alkoxyaryldiaralkylphosphine includes:
o-methoxyphenyldibenzylphosphine and
p-methoxyphenyldibenzylphosphine.

The (dialkoxyaryl)diarylphosphine includes 2,6-dimethoxyphenyldiphenylphosphine.

The amount used of the tertiary phosphine is preferably from 0.001 to 0.5 mole, more preferably from 0.01 to 0.1 mole, furthermore preferably from 0.02 to 0.08 mole, and especially preferably from 0.025 to 0.06 mole, per 1 mole of silica gel used in step (a).

The molar ratio of the amounts used between the silane compound having a haloalkyl group or a haloaryl group used in step (a) and the tertiary phosphine [ silane compound]/ [tertiary phosphine] is preferably from 0.1 to 15, more preferably from 0.1 to 7.5, furthermore preferably from 0.1 to 1.2, still more preferably from 0.2 to 1.0, even more preferably from 0.3 to 0.9, and especially preferably from 0.4 to 0.9 from the viewpoint of catalytic activity.

Moreover, step (b) is preferably carried out in a solvent, and a hydrocarbon solvent is preferred as the solvent. The hydrocarbon solvent includes a solvent similar to one used in the above step (a), and may be used alone or in combination of two or more thereof.

The solvent used in step (a) can also directly be used as the solvent of step (b), whereby the procedures of removal and drying of the solvent is not required. Thereby, it is possible to obtain the catalyst more easily.

Whereas the amount used of the solvent is not particularly limited, it is usually from 100 to 2,000 parts by mass, preferably from 100 to 1,750 parts by mass, and more preferably from 500 to 1,500 parts by mass, per 100 parts by mass of the tertiary phosphine.

The reaction temperature in step (b) is not particularly limited; however, it is preferably from 60 to 160° C., more preferably from 100 to 150° C., further more preferably from 110 to 140° C., from the viewpoint of reaction efficiency and suppression of catalyst deterioration due to heat.

Whereas the reaction time in step (b) is not particularly limited, it is preferably from 10 to 100 hours, more preferably from 15 to 50 hours, from the viewpoint of maintaining a sufficient phosphorus content and suppressing an elimination amount of the halogen.

In each step described above, the isolation of the catalyst precursor and catalyst may be performed as needed by appropriately combining the conventional means such as filtration, washing, and drying.

Whereas the molar ratio of the halogen content and the phosphorus content [halogen]/[phosphorus] in the catalyst for cyclic carbonate synthesis, obtained in step (b), is from 0.8 to 1.6, such a ratio is preferably from 1.0 to 1.6 from the viewpoint of catalyst activity and suppression of the occurrence of byproducts in cyclic carbonate synthesis.

When the molar ratio [halogen]/[phosphorus] exceeds 1.6, the catalytic activity is lowered due to the excess amount of remaining halogen, and byproducts also tend to easily occur during the synthesis of cyclic carbonates.

The above molar ratio [halogen/phosphorus] can be controlled by adjusting the amounts used of the silane compound having a haloalkyl group or a haloaryl group and a tertiary phosphine, and adsorbed water of the silica gel.

Further, the halogen content in the catalyst for cyclic carbonate synthesis is preferably from 0.25 to 0.8 mmol, more preferably from 0.3 to 0.8 mmol, per 1 g of the catalyst in view of catalytic activity and suppression of the occurrence of byproducts in the synthesis of cyclic carbonates.

By adjusting the amount used of the silane compound having a haloalkyl group or a haloaryl group and the amount of adsorbed water of the silica gel, the halogen content can be controlled within the above range.

The phosphorus content in the catalyst for cyclic carbonate synthesis is preferably from 0.25 to 0.6 mmol, more preferably from 0.3 to 0.6 mmol, per 1 g of the catalyst, in view of catalytic activity. The phosphorus content can be controlled within the above range by adjusting the amount used of the tertiary phosphine.

The catalyst for cyclic carbonate synthesis is a heterogeneous catalyst (solid catalyst) having pores. The average pore diameter is preferably from 1 to 50 nm, more preferably from 3 to 20 nm, further more preferably from 3.5 to 15 nm, still more preferably from 5 to 15 nm, and even more preferably from 6 to 15 nm.

Moreover, the specific surface area of the catalyst for cyclic carbonate synthesis is preferably from 80 to 2,000 $m^2/g$, more preferably from 100 to 1,000 $m^2/g$.

The content of the halogen and phosphorus, average pore diameter, and specific surface area may be measured in the same manner as in Example below.

Then, according to the production method of the present invention, a heterogeneous catalyst exhibiting an excellent catalytic activity for synthesizing cyclic carbonates in a high conversion rate, a high selectivity and a high yield can be produced in a simple way and at a low cost. Further, when synthesizing a cyclic carbonate by using the catalyst obtained in such a production method, there is little formation of byproducts such as bromopropanol and bromoethanol.

The catalyst of the present invention is useful as a catalyst for use in synthesizing a cyclic carbonate by reacting an epoxide with carbon dioxide.

<Synthesis Method of Cyclic Carbonate>

The synthesis method of cyclic carbonates according to the present invention comprises reacting an epoxide with carbon dioxide in the presence of a catalyst obtained by the above production method. The synthesis method may be conducted by a conventional method, but using the catalyst.

The amount used of the catalyst may be appropriately adjusted, and is usually from 0.01 to $10^6$ parts by mass, preferably from 0.1 to $10^5$ parts by mass, more preferably from 1 to $10^4$ parts by mass, per 100 parts by mass of the epoxide.

Moreover, the epoxide is not particularly limited as long as it is a compound containing at least one epoxy ring (three-membered ring consisting of two carbon atoms and one oxygen atom) in the structural formula, and includes, for example, ethylene oxide, propylene oxide, butylene oxide, isobutylene oxide, vinyl ethylene oxide, trifluoromethylethylene oxide, cyclohexene oxide, styrene oxide, butadiene monoxide, butadiene dioxide, 2-methyl-3-phenylbutene oxide, pinene oxide, and tetracyanoethylene oxide.

Among such epoxides, those represented by the following formula (3) are preferred.

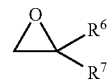

(3)

In the formula (3), $R^6$ and $R^7$ each independently represent a hydrogen atom, an alkyl group having 1 to 6 of carbon atom, a haloalkyl group having 1 to 6 of carbon atom, an alkenyl group having 2 to 6 of carbon atom, or a haloalkenyl group having 2 to 6 of carbon atom.

The number of carbon atom in the alkyl group and the haloalkyl group represented by $R^6$ and $R^7$ is preferably 1 to 4. Examples of the alkyl group include groups similar to those as defined for $R^2$. Halogen atom in the haloalkyl group includes a halogen similar to that as defined in X.

Among those represented by the formula (3), ethylene oxide and propylene oxide are preferred.

The synthesis method for cyclic carbonates according to the present invention may be carried out either in the presence or absence of a solvent. If the solvent is used, other than cyclic carbonates as the target compound, it includes, for example, aliphatic hydrocarbons (e.g. pentane, hexane, and heptane); aromatic hydrocarbons (e.g. benzene and toluene); alcohols (e.g. methanol and ethanol); ketone (e.g. acetone and methyl ethyl ketone); ethers (e.g. diethyl ether, methyl-tert-butyl ether, tetrahydrofuran, and dioxane); amides (e.g. dimethylformamide and dimethylacetamide); esters (e.g. ethyl acetate); tertiary amines (e.g. triethylamine, pyridine, methylpyridazine, N,N'-dimethylpyridazinone); sulfides (e.g. dibutyl sulfide); and phosphines (e.g. tributylphosphine). The solvent may be used alone or in combination of two or more thereof.

The reaction temperature of the synthesis method for a cyclic carbonate according to the present invention is preferably from 20 to 160° C., more preferably from 50 to 150° C., furthermore preferably from 80 to 140° C., from the viewpoint of reaction efficiency.

Whereas the reaction pressure is not particularly limited, it is preferably from 0.1 to 100 MPa, more preferably from 0.5 to 50 MPa, further more preferably from 1.0 to 25 MPa.

In addition, whereas the reaction time is not particularly limited, it is usually from 0.1 to 10 hours, preferably from 0.5 to 5 hours.

Further, the synthesis method of the cyclic carbonate of the present invention can adopt a technique that is commonly used as a reaction mode, such as a stirring system or a fixed bed system. The reaction may be attained in any method of a batch type process, a semi-batch type process, and a continuous flow type process.

The batch type process is performed, for example, in the following manner. An epoxide and a catalyst are charged into an autoclave equipped with a stirring device. The autoclave is filled with carbon dioxide and then sealed. Subsequently, the autoclave is heated to a predetermined temperature while stirring the mixture in the autoclave, and further filled with carbon dioxide, thereby adjusting the internal pressure to a predetermined pressure. After the reaction for a predetermined period of time, the produced cyclic carbonate is separated by a desired means.

The continuous flow type process is performed as shown in FIG. 1. Using for example a flow type reaction system (FIG. 1) integrated with high-pressure fluid feed pumps (A, B), a fluid mixer (C), a column reactor (D), a pressure controller (E) and a temperature controller (F), and the like, an epoxide and carbon dioxide are mixed together, then heated in the column reactor (D) filled with a catalyst, and continuously reacted therein. A substance that could be a solvent except the starting materials epoxide and carbon dioxide may be introduced into the reactor along with the starting materials.

Whereas pretreatment of the catalyst is not particularly required, it is possible to improve the yield of the cyclic carbonate if evacuation is performed at from 20 to 140° C., preferably from 50 to 120° C., prior to the reaction or if treatment is performed in an inert gas stream such as helium, argon, nitrogen, or carbon dioxide.

According to the synthesis method of a cyclic carbonate of the present invention, it is possible to synthesize a cyclic carbonate in which the epoxy ring of the epoxide is converted into a carbonate ring (5-membered ring having an O—CO—O bond). Such a cyclic carbonate includes, for example, ethylene carbonate, propylene carbonate, butylene carbonate, isobutylene carbonate, trifluoromethylethylene carbonate, vinyl ethylene carbonate, cyclohexene carbonate, styrene carbonate, butadiene monocarbonate, butadiene dicarbonate, chloromethyl carbonate, pinene carbonate, and tetracyanoethylene carbonate.

The present invention provides a method for synthesizing a cyclic carbonate, comprising reacting an epoxide with carbon dioxide with use of a silica gel-immobilized phosphonium salt halide as a catalyst containing a quaternary phosphonium group having a halide anion as the counterion, said catalyst having the halogen content of from 0.25 to 0.8 mmol per 1 g of the catalyst and having the molar ratio of the halogen content and the phosphorus content [halogen/phosphorus] of from 1.0 to 1.6. The catalyst used in the synthesis method is produced by the production method of a catalyst for the synthesis of a cyclic carbonate according to the present invention. Moreover, the synthesis method of the cyclic carbonates may be performed in the same manner as in the method for synthesizing a cyclic carbonate with use of the catalyst that is obtained by the method for producing a catalyst to synthesize a cyclic carbonate of the present invention.

A according to these synthesis methods of a cyclic carbonate of the present invention, it is possible to synthesize a cyclic carbonate in a high conversion rate and a high selectivity with a high yield. In the synthesis method, there is also little formation of byproducts such as bromopropanol and 2-bromoethanol.

EXAMPLES

Hereinafter, the present invention is described in more detail with reference to Examples, which, however, are not intended to restrict the scope of the invention. The average pore diameter, specific surface area, and particle diameter (or particle size) of silica gel are manufacturer's nominal values.

Analytical methods used in each Example and Comparative Example are as follows.

(1) In the production of the catalyst, the bromine-modified amount and the phosphorus-modified amount were measured using the fluorescent X-ray analysis (apparatus: product name "System 3270" (manufactured by Rigaku Industrial Co.), measurement conditions: Rh tube, tube voltage 50 kV, tube current 50 mV, vacuum atmosphere, detector: SC, F-PC).

(2) In the synthesis of cyclic carbonates, analysis of the composition of the reaction solution was performed by using a gas chromatography. The analysis conditions were as follows.

Apparatus: product name "GC-2010 Plus" (manufactured by Shimadzu Corporation)
Detector: FID
INJ temperature: 150° C.
DET temperature: 260° C.
Amount of sample: 0.3 μL
Split ratio: 5
Column: DB-624 (60 m, 0.32 mmID, 1.8 μm, manufactured by Agilent Technologies)
Column temperature: 70° C., 3 minutes-5° C./minute-120° C.-10° C./minute-250° C., 5 minutes (31 minutes in total)

Example 1: Production of Catalyst A-1

(Production of Catalyst Precursor)

1.5 grams of bead silica gel (CARiACT Q-6 (average pore diameter 6 nm, particle diameter 1.2-2.4 mm, specific surface area 450 m$^2$/g), manufactured by Fuji Silysia Chemical Ltd.) and 5 mL of 2N hydrochloric acid were charged in a 20 mL-flask, and the atmosphere in the flask was substituted with nitrogen. Then, demetallation of the silica gel was carried out by heating to reflux for 4 hours. After that, the silica gel was separated by filtration and was sufficiently washed by using deionized water. Note that the washed solution did not become cloudy when 1N silver nitrate solution was dropwise added thereto. This confirmed that chlorine was not included in the solution after such washing, and enough washing had been performed. The silica gel after washing was placed in a 20-mL flask and subjected to vacuum drying at 180° C. for 5 hours, thereby to remove the moisture in the silica gel.

The acid-treated and dried silica gel and 7.5 mL of dehydrated toluene were charged into a 20 mL-flask and the inside of the flask was replaced with nitrogen. Then, 15 μL of water was added thereto with a microsyringe and the mixture was thoroughly stirred. The moisture concentration in toluene after stirring was found to be 180 ppm, and the amount of water adsorbed on the silica gel was found to be 0.94% by mass with respect to the silica gel.

To this was dropwise added 0.9 mL of 3-bromopropyltrimethoxysilane, and the mixture was directly heated under reflux at 110° C. for 5 hours, thereby to perform a silanization reaction. The resulting reaction product was separated by filtration and washed thoroughly with acetone. Incidentally, it was confirmed that the amount of 3-bromopropyltrimethoxysilane in the solution after washing was less than 50 ppm by gas chromatographic analysis. The obtained reaction product was placed in a 20 mL-flask and subjected to vacuum drying at 120° C. for 2 hours to yield a catalyst precursor (bromopropylated silica gel). Note that the measurement result on the Br-modified amount in the obtained catalyst precursor was found to be 0.88 mmol/g by the fluorescent X-ray analysis.

(Production of Catalyst)

The obtained catalyst precursor and 10 mL of xylene were charged into a 20 mL-flask, and after the inside of the flask was replaced with nitrogen, 0.9 g of tri-n-butylphosphine was dropwise added thereto. The mixture was directly subjected to quaternary phosphonium formation under heating to reflux at 140° C. for 45 hours. After the reaction, the resulting reaction product was separated by filtration and washed thoroughly with acetone. Incidentally, it was confirmed that the amount of tri(n-butyl)phosphine in the solution after washing was less than 50 ppm by gas chromatographic analysis. The obtained reaction product was placed in a 20 mL-flask and subjected to vacuum drying at 120° C. for 2 hours to yield a desired catalyst A-1 (silica gel surface-modified with tributylphosphonium bromide). The measurement results on the Br-modified amount and P-modified amount of the obtained catalyst are shown in Table 1.

Examples 2 to 4: Production of Catalysts A-2 to A-4

Catalysts were produced in the same manner as in Example 1, except that the added amount of water was changed to 0 μL (no addition), 1.0 μL, and 7.5 μL, respectively, from 15 μL and then analyzed. The results are shown in Table 1.

Comparative Examples 1 and 2: Production of Catalysts RA-1 and RA-2

Catalysts were produced in the same manner as in Example 1, except that the added amount of water was changed to 45 μL and 75 μL, respectively, from 15 μL and then analyzed. The results are shown in Table 1.

Example 5: Synthesis of Propylene Carbonate

Propylene carbonate was synthesized by a batch process, and the activity of the catalyst was evaluated.

That is, 800 mg of the catalyst A-1 prepared in Example 1 was charged into a 50 ml-autoclave equipped with a stirring bar, and subjected to vacuum drying at 120° C. for 1 hour. After the pressure in the autoclave was returned to the atmospheric pressure with nitrogen and the temperature was returned to room temperature, 3.5 g (60 mmol) of propylene oxide was charged thereinto. Subsequently, carbon dioxide was provisionally filled to 1.5 MPa, and heating to 100° C. was carried out while stirring the mixture in the autoclave with a rotor at 1,000 rpm. After the autoclave was further filled with carbon dioxide so as to adjust the internal pressure to 3 MPa, the mixture was subjected to a reaction for 1 hour. After cooling, the remaining carbon dioxide was released to depressurize the autoclave. The obtained reaction solution was analyzed by gas chromatography. The results are shown in Table 2.

Incidentally, propylene glycol, 2-bromopropanol, and 1-bromo-2-propanol were detected as reaction impurities in the gas chromatograph. The detection amounts of these bromopropanols were also shown in Table 2.

Examples 6 and 7: Synthesis of Propylene Carbonate

Propylene carbonate was synthesized by the batch type reaction in the same manner as in Example 5, except that the catalyst A-1 was changed to catalysts A-2 and A-4, respectively and then the catalytic activity was evaluated. The results are shown in Table 2.

Comparative Examples 3 and 4: Synthesis of Propylene Carbonate

Propylene carbonate was synthesized by the batch type reaction in the same manner as in Example 5, except that the catalyst A-1 was changed to catalysts RA-1 and RA-2, respectively, and then the catalytic activity was evaluated. The results are shown in Table 2.

TABLE 1

| | Catalyst | Amount of water added (μL) | Moisture concentration in toluene (ppm) | Amount of adsorbed water of silica gel (% by mass) | Precursor Catalyst (mmol/g) | Br content (mmol/g) | P content (mmol/g) | Br/P |
|---|---|---|---|---|---|---|---|---|
| Example 1 | A-1 | 15 | 180 | 0.94 | 0.88 | 0.70 | 0.49 | 1.4 |
| Example 2 | A-2 | 0 | 14 | 0 | 0.85 | 0.69 | 0.52 | 1.3 |
| Example 3 | A-3 | 1.0 | 26 | 0.06 | 0.87 | 0.71 | 0.55 | 1.3 |
| Example 4 | A-4 | 7.5 | 94 | 0.46 | 0.85 | 0.69 | 0.54 | 1.3 |
| Comparative Example 1 | RA-1 | 45 | 245 | 2.8 | 1.02 | 0.85 | 0.54 | 1.6 |
| Comparative Example 2 | RA-2 | 75 | 266 | 4.9 | 1.12 | 0.97 | 0.61 | 1.6 |

TABLE 2

| | Catalyst | Moisture concentration in toluene (ppm) | Amount of adsorbed water of silica gel (% by mass) | Results of batch reaction | | | |
|---|---|---|---|---|---|---|---|
| | | | | Conversion rate (mmol/g) | Selectivity (mmol/g) | Yield (mmol/g) | Detected amount of BrOH*[1] (μmol) |
| Example 5 | A-1 | 180 | 0.94 | 60 | 99.4 | 60 | 98 |
| Example 6 | A-2 | 14 | 0 | 61 | 99.4 | 60 | 104 |
| Example 7 | A-4 | 94 | 0.46 | 60 | 99.5 | 60 | 90 |
| Comparative Example 3 | RA-1 | 245 | 2.8 | 53 | 99.4 | 53 | 124 |
| Comparative Example 4 | RA-2 | 266 | 4.9 | 43 | 99.2 | 42 | 145 |

*[1] 2-Bromopropanol and 1-bromo-2-propanol

Example 8: Production of Catalyst B-1

(Production of Catalyst Precursor)

Sixty grams of bead silica gel (CARiACT Q-6 (average pore diameter 6 nm, particle diameter 1.2-2.4 mm, specific surface area 450 m$^2$/g), manufactured by Fuji Silysia Chemical Ltd.) and 150 mL of 2N hydrochloric acid were charged into a 500 mL three-necked flask equipped with a stirring blade, and the atmosphere of the inside of the flask was substituted with nitrogen. Then, demetallation of the silica gel was carried out by heating to reflux for 4 hours. After that, the silica gel was separated by filtration and was sufficiently washed by using deionized water. The washed solution did not become cloudy when 1N silver nitrate solution was dropwise added thereto. This confirmed that chlorine was not included in the solution, and enough washing had been performed.

The acid-treated silica gel and 150 mL of toluene were charged into a 500 mL three-necked flask equipped with a Dean-Stark trap and a stirring blade, and the mixture was subjected to azeotropic dehydration of toluene and water under reflux at 110° C. for 2 hours, thereby removing the moisture in the silica gel.

Note that the moisture concentration in toluene at this time was 53 ppm, and the amount of water adsorbed on the silica gel was 1% by mass or less relative to the silica gel.

Then, the Dean-Stark trap was removed, and the atmosphere in the flask was replaced with nitrogen, after which 14 g of 3-bromopropyltrimethoxysilane was dropwise added. The mixture was directly heated under reflux at 110° C. for 5 hours, thereby performing silanization reaction.

The resulting reaction product was separated by filtration and washed thoroughly with acetone. Incidentally, it was confirmed that the amount of 3-bromopropyltrimethoxysilane in the solution after washing was less than 50 ppm by gas chromatographic analysis. The obtained reaction product was placed in a 500 mL-flask and subjected to vacuum drying at 120° C. for 2 hours to yield 69 g of a catalyst precursor PB-1 (bromopropylated silica gel). The measurement result of the Br-modified amount in the obtained catalyst precursor was 0.77 mmol/g by X-ray fluorescence analysis.

(Production of Catalyst)

The obtained catalyst precursor PB-1 (1.5 g) and 10 mL of xylene were charged into a 20 mL-flask, and after the inside of the flask was replaced with nitrogen, 0.8 mL of tri-n-butylphosphine was dropwise added thereto. The mixture was directly subjected to quaternary phosphonium formation under heating to reflux at 135° C. for 20 hours. After the reaction, the resulting reaction product was separated by filtration and washed thoroughly with acetone. It was confirmed that the amount of tri-n-butylphosphine in the solution after washing was less than 50 ppm by gas chromatographic analysis. The obtained reaction product was placed in a 20 mL-flask and subjected to vacuum drying at 120° C. for 2 hours to yield a desired catalyst B-1 (silica gel surface-modified with tributylphosphonium bromide). The measurement results on the Br-modified amount and P-modified amount in the resulting catalyst are shown in Table 3.

Example 9: Production of Catalyst B-2

A catalyst B-2 was produced in the same manner as in Example 8, except that the heating time after dropwise addition of tri-n-butylphosphine was changed to 45 hours from 20 hours. The results are shown in Table 3.

Example 10: Production of Catalyst B-3

A catalyst B-3 was produced in the same manner as in Example 8, except that the reaction solvent was changed to n-dodecane from xylene. The results are shown in Table 3.

Example 11: Production of Catalyst B-4

A catalyst B-4 was produced in the same manner as in Example 10, except that the heating time after dropwise addition of tri-n-butylphosphine was changed to 45 hours from 20 hours. The results are shown in Table 3.

Example 12: Production of Catalyst B-5

A catalyst B-5 was produced in the same manner as in Example 8, except that the reaction solvent was changed to toluene from xylene, the reaction temperature was changed to 110° C. from 135° C., and the heating time was changed to 1 day from 20 hours, respectively. The results are shown in Table 3.

Example 13: Production of Catalyst B-6

A catalyst B-6 was produced in the same manner as in Example 12, except that the heating time was changed to 3 days from 20 hours. The results are shown in Table 3.

Examples 14 to 19: Synthesis of Propylene Carbonate

Propylene carbonate was synthesized by the batch type reaction in the same manner as in Example 5, except that the catalyst A-1 was changed to catalysts B-1 to B-6, and then the catalytic activity was evaluated. The results are shown in Table 3.

gel). The measurement result of the Br-modified amount in the obtained catalyst precursor was 0.72 mmol/g by the fluorescent X-ray analysis.

TABLE 3

|  | Catalyst | Amount of adsorbed water of silica gel (% by mass) | Fluorescent X-ray analysis Catalyst | | | Results of batch reaction | | | |
|---|---|---|---|---|---|---|---|---|---|
|  |  |  | Br content (mmol/g) | P content (mmol/g) | Br/P | Conversion rate (%) | Selectivity (%) | Yield (%) | Detected amount of BrOH*1 (μmol) |
| Examples 8, 14 | B-1 | ≤1 | 0.70 | 0.46 | 1.5 | 61 | 99.5 | 61 | 119 |
| Examples 9, 15 | B-2 | ≤1 | 0.71 | 0.45 | 1.6 | 68 | 99.6 | 68 | 126 |
| Examples 10, 16 | B-3 | ≤1 | 0.70 | 0.49 | 1.4 | 62 | 99.6 | 61 | 101 |
| Examples 11, 17 | B-4 | ≤1 | 0.68 | 0.56 | 1.2 | 60 | 99.5 | 60 | 101 |
| Examples 12, 18 | B-5 | ≤1 | 0.73 | 0.48 | 1.5 | 65 | 99.5 | 65 | 128 |
| Examples 13, 19 | B-6 | ≤1 | 0.70 | 0.52 | 1.4 | 65 | 99.5 | 65 | 101 |

*1 2-Bromopropanol and 1-bromo-2-propanol

Example 20: Production of Catalyst C-1

(Production of Catalyst Precursor)

One hundred grams of bead silica gel (CARiACT Q-6 (average pore diameter 6 nm, particle diameter 1.2-2.4 mm, specific surface area 450 m$^2$/g), manufactured by Fuji Silysia Chemical Ltd.) and 250 mL of 2N hydrochloric acid were charged into a 1 L three-necked flask equipped with a stirring blade, and the atmosphere of the inside of the flask was substituted with nitrogen. Then, demetallation of the silica gel was carried out by heating to reflux for 4 hours. After that, the silica gel was separated by filtration and was sufficiently washed by using deionized water. The washed solution did not become cloudy when 1N silver nitrate solution was dropwise added thereto. This confirmed that chlorine was not included in the solution after such washing, and enough washing had been performed.

The acid-treated silica gel and 250 mL of toluene were charged into a 1 L three-necked flask equipped with a Dean-Stark trap and a stirring blade, and the mixture was subjected to azeotropic dehydration of toluene and water under reflux at 110° C. for 2 hours, thereby removing the moisture in the silica gel.

The moisture concentration in toluene at this time was 20 ppm, and the amount of water adsorbed on the silica gel was 1% by mass or less relative to the silica gel.

Next, the Dean-Stark trap was removed from the 1 L three-necked flask equipped with a stirring blade, and the atmosphere in the flask was replaced with nitrogen, after which 24 g of 3-bromopropyltrimethoxysilane was dropwise added to the flask. The mixture was directly heated under reflux at 110° C. for 5 hours so that the silanization reaction was carried out.

Subsequently, the resulting reaction product was separated by filtration and washed five times with acetone. Incidentally, it was confirmed that the amount of 3-bromopropyltrimethoxysilane in the solution after washing was less than 50 ppm by gas chromatographic analysis. The obtained reaction product was placed in a 1 L-flask and subjected to vacuum drying at 120° C. for 2 hours to yield 112 g of a catalyst precursor PC-1 (bromopropylated silica gel). The measurement result of the Br-modified amount in the obtained catalyst precursor was 0.72 mmol/g by the fluorescent X-ray analysis.

(Production of Catalyst)

The obtained catalyst precursor PC-1 and 350 mL of xylene were charged into a 1 L three-necked flask equipped with a stirring blade, and after the inside of the flask was replaced with nitrogen, 22 g of tri-n-butylphosphine was dropwise added thereto. The mixture was directly subjected to quaternary phosphonium formation under heating to reflux at 140° C. for 25 hours. After the reaction, the reaction product was separated by filtration and washed three times with acetone. It was confirmed that the amount of tri-n-butylphosphine in the solution obtained after washing three times was less than 50 ppm by gas chromatographic analysis. The obtained reaction product was placed in a 1 L-flask and subjected to vacuum drying at 120° C. for 2 hours to yield 124 g of a desired catalyst C-1 (tributylphosphonium bromide-surface modified silica gel). The measurement results on the Br-modified amount and P-modified amount in the resulting catalyst are shown in Table 4.

Example 21: Synthesis of Propylene Carbonate

Propylene carbonate was synthesized by the batch type reaction and the catalytic activity of the catalyst C-1 was evaluated.

That is, the catalyst C-1 (200 mg) prepared in Example 20 was charged into a 50 ml-autoclave equipped with a stirring bar, and subjected to vacuum drying at 120° C. for 1 hour. After the pressure in the autoclave was returned to the atmospheric pressure with nitrogen and the temperature was returned to room temperature, 3.5 g (60 mmol) of propylene oxide was charged thereinto. Subsequently, carbon dioxide was provisionally filled to 1.5 MPa, and then heating to 120° C. was carried out while stirring the mixture in the autoclave with a rotor at 1,000 rpm. After the autoclave was further filled with carbon dioxide so that the internal pressure was adjusted to 3.5 MPa, the reaction was performed for 1 hour. After cooling, the remaining carbon dioxide was released to depressurize the autoclave. The resulting reaction solution was analyzed by gas chromatography. The results are shown in Table 4.

Incidentally, propylene glycol, 2-bromopropanol and 1-bromo-2-propanol were detected as impurities in the gas chromatograph. The detected amounts of these bromopropanols were also shown in Table 4.

Example 22: Synthesis of Ethylene Carbonate

Synthesis of ethylene carbonate was carried out by a batch process, and the activity of the catalyst C-1 was evaluated.

That is, 200 mg of the catalyst C-1 prepared in Example 20 was charged into a 50 ml-autoclave equipped with a stirring bar, and subjected to vacuum drying at 120° C. for 1 hour. After the pressure in the autoclave was returned to the atmospheric pressure with nitrogen and the temperature was returned to room temperature, 2.8 g (60 mmol) of ethylene oxide was charged thereinto. Subsequently, carbon dioxide was provisionally filled therein to 1.5 MPa, and heating to 120° C. was carried out while stirring the mixture in the autoclave with a rotor at 1000 rpm. After the autoclave was further filled with carbon dioxide so that the internal pressure was adjusted to 3.5 MPa, the reaction was performed for 1 hour. After cooling, the remaining carbon dioxide was released to depressurize the autoclave. Since the resulting ethylene carbonate has a melting point of 36° C., 4 g of acetonitrile solvent was added to the autoclave so that the reaction mixture was dissolved. The resulting reaction solution was analyzed by gas chromatography. The results are shown in Table 4.

Incidentally, ethylene glycol, diethylene glycol, and 2-bromopropanol were detected as impurities. The detection amount of 2-bromoethanol was also shown in Table 4.

dropwise added to the flask. The mixture was directly heated under reflux at 135° C. for 7 hours so as to perform the silanization reaction.

Subsequently, the resulting reaction product was separated by filtration and washed twice with xylene to obtain 3810 g of a catalyst precursor (bromopropylated silica gel) containing xylene.

It was confirmed that the amount of 3-bromopropyltrimethoxysilane in the solution after two times washing was less than 50 ppm by the gas chromatographic analysis. The measurement result of the Br-modified amount in the obtained catalyst precursor was 0.38 mmol/g by the fluorescent X-ray analysis. Incidentally, the content of xylene was 57% by mass and the obtained precursor was estimated to be about 2170 g.

(Production of Catalyst)

The obtained catalyst precursor and 5000 mL of xylene were charged into a 10 L three-necked flask equipped with a stirring blade, and after the inside of the flask was replaced with nitrogen, 453 g of tri-n-butylphosphine was dropwise added thereto. The mixture was directly subjected to quaternary phosphonium formation under heating at 120° C. for 25 hours. After the reaction, the reaction product was separated by filtration and washed six times with acetone. Incidentally, it was confirmed that the amount of tri-n-butylphosphine in the solution after six times washing was less than 50 ppm by the gas chromatographic analysis. The obtained reaction product was subjected to vacuum drying in a stream of nitrogen at 120° C. for 5 hours to yield 2,328 g of a desired catalyst D-1 (tributylphosphonium bromide-

TABLE 4

|  | Catalyst | Amount of adsorbed water of silica gel (% by mass) | Fluorescent X-ray analysis Catalyst | | | Results of batch reaction | | | | |
|---|---|---|---|---|---|---|---|---|---|---|
|  |  |  | Br content (mmol/g) | P content (mmol/g) | Br/P | Reaction substrate | Conversion rate (%) | Selectivity (%) | Yield (%) | Detected amount of BrOH*[4] (μmol) |
| Examples 20, 21 | C-1 | ≤1 | 0.58 | 0.43 | 1.3 | PO*[2] | 32 | 99.8 | 32 | 23 |
| Examples 20, 22 |  |  |  |  |  | EO*[3] | 39 | 99.8 | 39 | 13 |

*[2]Propylene oxide;
*[3]Ethylene oxide;
*[4]Bromopropanol (2-bromopropanol and 1-bromo-2-propanol) or 2-bromoethanol Example 23: Production of Catalyst D-1

(Production of Catalyst Precursor)

Bead silica gel (2,000 g) (CARiACT Q-10 (average pore diameter 10 nm, particle diameter 1.2-2.4 mm, specific surface area 300 m$^2$/g), manufactured by Fuji Silysia Chemical Ltd.) and 5000 mL of xylene were charged into a 10 L three-necked flask equipped with a Dean-Stark trap and a stirring blade, and azeotropic dehydration of xylene-water was carried out under reflux at 140° C. for 2 hours to remove the moisture in the silica gel.

The moisture concentration in xylene at this time was 14 ppm, and the amount of water adsorbed on the silica gel was 1% by mass or less relative to the silica gel.

Then, the Dean-Stark trap was removed, and the atmosphere in the flask was replaced with nitrogen, after which 219 g (0.846 mmol) of 3-bromopropyltrimethoxysilane was surface modified silica gel). The Br-modified amount in the obtained catalyst was 0.35 mmol/g, the P-modified amount was 0.32 mmol/g, and the ratio of Br/P was 1.1.

Comparative Example 5: Production of Catalyst RD-1

A catalyst was produced in the same manner as in Patent Literature 3.

That is, 7.00 g of a 3-bromopropyl-functionalized silica gel (functionalization rate 1.54 mmol/g, particle diameter 200-400 mesh) (manufactured by Aldrich Co., Ltd.) was suspended in 50 ml of toluene under an argon atmosphere, and 3.00 g of tributylphosphine was added thereto while slowly stirring in a 200 ml three-necked flask equipped with a stirring blade. Then, the suspension was allowed to react at 110° C. for one week while stirring under an argon atmosphere. The suspension after the reaction was filtered to remove the liquid and the resulting solid was washed successively with methanol, acetone, and ether, dried in the air and dried at room temperature for 6 hours under a vacuum of 1 mm or less, thereby obtaining a catalyst RD-1. The measurement results on the Br-modified amount and P-modified amount in the obtained catalyst are shown in Table 5.

Example 24: Synthesis of Ethylene Carbonate

Ethylene carbonate was synthesized by the following batch type process and the catalytic activity of the powdered catalyst D-1 was evaluated.

First, the catalyst D-1 prepared in Example 23 was ground in a mortar, and the resulting powder was sieved to collect ones having a particle diameter of 200-400 mesh.

Then, 800 mg of the powdered catalyst D-1 was charged into a 50 ml-autoclave equipped with a stirring bar, and subjected to vacuum drying at 120° C. for 1 hour. After returning the pressure in the autoclave to the atmospheric pressure with nitrogen and the temperature to room temperature, 2.8 g (60 mmol) of ethylene oxide was charged thereinto. Subsequently, carbon dioxide was provisionally filled therein to 1.5 MPa, and heating to 100° C. was carried out while stirring the mixture in the autoclave with a rotor at 1000 rpm. After the autoclave was further filled with carbon dioxide so as to adjust the internal pressure to 5.0 MPa, the reaction was performed for 1 hour. After cooling, the remaining carbon dioxide was released to depressurize the autoclave. Since the resulting ethylene carbonate has a melting point of 36° C., 4 g of acetonitrile solvent was added to the autoclave so that the reaction mixture was dissolved. The resulting reaction solution was analyzed by gas chromatography to evaluate the catalytic activity. The results are shown in Table 5.

Comparative Example 6: Synthesis of Ethylene Carbonate

Ethylene carbonate was synthesized by the batch type reaction in the same manner as in Example 24, except that the powdered catalyst D-1 was changed to a catalyst RD-1, and then the catalytic activity was evaluated. The results are shown in Table 5.

The invention claimed is:

1. A method for producing a catalyst for cyclic carbonate synthesis, the method comprising:
   (a) obtaining a catalyst precursor comprising a haloalkyl group X—$R^1$— by reacting a silane compound comprising the haloalkyl group with a silica gel having an amount of adsorbed water of 1% by mass or less wherein the silane compound is of formula (1):

wherein $R^1$ is a linear or branched alkylene group having 2 to 8 carbon atoms;
   wherein $R^2$ is an alkyl group having 1 to 4 carbon atoms, and
   wherein X is a halogen atom, and
   (b) reacting the catalyst precursor with a tertiary phosphine to obtain the catalyst for cyclic carbonate synthesis wherein the tertiary phosphine is of formula (2):

wherein $R^3$ to $R^5$ each independently represent an alkyl group having 1 to 8 carbon atoms,
   wherein a molar ratio of a halogen content to a phosphorus content [halogen]/[phosphorus] in the catalyst for cyclic carbonate synthesis is from 1.0 to 1.6, and
   wherein the halogen content in the catalyst for cyclic carbonate synthesis is from 0.25 to 0.8 mmol per 1 g of the catalyst,
   wherein the obtaining (a) and the reacting (b) are carried out in a hydrocarbon solvent selected from the group consisting of toluene, xylene and ethylbenzene.

2. The method according to claim 1, wherein the amount of adsorbed water of the silica gel used in the obtaining (a) is from 0.001 to 0.9% by mass.

3. A method for synthesizing a cyclic carbonate, the method comprising:
   reacting an epoxide with carbon dioxide in the presence of a silica gel-immobilized phosphonium salt halide as a catalyst comprising a quaternary phosphonium group and a halide anion as a counterion,

TABLE 5

| | Catalyst | Catalyst shape | Amount of adsorbed water of silica gel (% by mass) | Fluorescent X-ray analysis Catalyst | | | Results of batch reaction | | | Detected |
| --- | --- | --- | --- | --- | --- | --- | --- | --- | --- | --- |
| | | | | Br content (mmol/g) | P content (mmol/g) | Br/P | Conversion rate (%) | Selectivity (%) | Yield (%) | amount of BrOH*5 (μmol) |
| Examples 24 | D-1 | Powder | ≤1 | 0.35 | 0.32 | 1.1 | 94 | 99.8 | 94 | 32 |
| Comparative Examples 5, 6 | RD-1 | Powder | — | 0.85 | 0.49 | 1.7 | 86 | 99.6 | 86 | 142 |

*5 2-Bromoethanol

As shown in the above Examples, by using the catalyst obtained according to the production method of the present invention, cyclic carbonates can be synthesized in a high conversion rate and a high yield, and it is also possible to suppress the generation of impurities such as bromopropanol and 2-bromoethanol.

wherein the catalyst has a halogen content of from 0.25 to 0.8 mmol per 1 g of the catalyst and has a molar ratio of the halogen content to a phosphorus content [halogen]/[phosphorus] in the catalyst for cyclic carbonate synthesis of from 1.0 to 1.6, wherein the silica gel-immobilized phosphonium salt halide as a catalyst comprising a quaternary phosphonium group and a halide anion as a counterion is obtained by
(a) reacting a silane compound comprising a haloalkyl group X—R¹— with a silica gel having an amount of adsorbed water of 1% by mass or less to form a catalyst precursor wherein the silane compound in the reacting (a) is of formula (1):

wherein R¹ is a linear or branched alkylene group having 2 to 8 carbon atoms;
wherein R² is an alkyl group having 1 to 4 carbon atoms, and
wherein X is a halogen atom, then
(b) reacting the catalyst precursor with a tertiary phosphine to obtain the catalyst for cyclic carbonate synthesis wherein the tertiary phosphine in the reacting (b) is of formula (2):

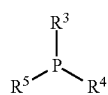

wherein R³ to R⁵ each independently represent an alkyl group having 1 to 8 carbon atoms, wherein the reacting (a) and the reacting (b) are carried out in a hydrocarbon solvent selected from the group consisting of toluene, xylene and ethylbenzene.

4. The method according to claim 3, wherein the epoxide is one or more members selected from the group consisting of ethylene oxide and propylene oxide.

5. The method according to claim 1, wherein the reacting (b) is carried out in toluene.

6. The method of claim 1, further comprising:
demetallating the silica gel before the obtaining (a).

7. The method according to claim 1, wherein the reacting (b) is carried out at a temperature of from 100 to 150° C.

8. The method according to claim 1, wherein the reacting (b) is carried out in a refluxing hydrocarbon solvent selected from the group consisting of toluene, xylene and ethylbenzene.

9. The method according to claim 1, wherein the phosphorous content is from 0.3 to 0.6 mmol per 1 g of the catalyst.

10. The method according to claim 3, wherein the reacting (b) is carried out in toluene.

11. The method according to claim 3, wherein the reacting (b) is carried out at a temperature of from 100 to 150° C.

12. The method according to claim 3, wherein the reacting (b) is carried out in a refluxing hydrocarbon solvent selected from the group consisting of toluene, xylene and ethylbenzene.

13. The method according to claim 3, wherein the phosphorous content of the catalyst is from 0.3 to 0.6 mmol per 1 g of the catalyst.

* * * * *